(12) United States Patent
Bente, IV et al.

(10) Patent No.: US 9,016,144 B2
(45) Date of Patent: **\*Apr. 28, 2015**

(54) SENSOR ASSEMBLY AND MEDICAL DEVICE INCORPORATING SAME

(71) Applicant: Medtronic MiniMed, Inc., Northridge, CA (US)

(72) Inventors: Paul F. Bente, IV, Wayne, PA (US); Pablo Vazquez, Granada Hills, CA (US); Ian B. Hanson, Wayne, PA (US); Afshin Bazargan, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 13/904,687

(22) Filed: May 29, 2013

(65) Prior Publication Data

US 2013/0255400 A1    Oct. 3, 2013

Related U.S. Application Data

(63) Continuation of application No. 12/908,807, filed on Oct. 20, 2010, now Pat. No. 8,474,332.

(51) Int. Cl.
*G01L 1/04* (2006.01)
*G01L 1/06* (2006.01)
*A61M 5/142* (2006.01)
*G01L 1/22* (2006.01)
*G01L 1/26* (2006.01)

(52) U.S. Cl.
CPC ............... *G01L 1/06* (2013.01); *A61M 5/14248* (2013.01); *A61M 2205/332* (2013.01); *G01L 1/2231* (2013.01); *G01L 1/26* (2013.01)

(58) Field of Classification Search
CPC ................... A61M 2205/332; A61B 18/1492; G01L 1/26
USPC ................................ 73/760, 862.53, 862.627
See application file for complete search history.

(56) References Cited

U.S. PATENT DOCUMENTS

| | | | | |
|---|---|---|---|---|
| 4,418,326 | A * | 11/1983 | Delapierre | 338/5 |
| 6,616,667 | B1 * | 9/2003 | Steiger et al. | 606/916 |
| 7,936,458 | B2 * | 5/2011 | Saha | 356/364 |
| 8,474,332 | B2 * | 7/2013 | Bente et al. | 73/862.53 |

* cited by examiner

*Primary Examiner* — Max Noori
(74) *Attorney, Agent, or Firm* — Ingrassia Fisher & Lorenz, P.C.

(57) ABSTRACT

Apparatus are provided for sensor assemblies and related medical devices. An embodiment of a sensor assembly includes a beam and a sensing element disposed on the beam. The sensor assembly also includes a structure to prevent deflection of the beam when a force applied to the sensor assembly is greater than a threshold value.

20 Claims, 10 Drawing Sheets

SENSOR ASSEMBLY AND MEDICAL DEVICE INCORPORATING SAME

CROSS-REFERENCE TO RELATED APPLICATIONS

This application is a continuation of U.S. patent application Ser. No. 12/908,807, filed Oct. 20, 2010. The subject matter described herein is also related to the subject matter described in U.S. patent application Ser. No. 12/908,809 and U.S. patent application Ser. No. 12/908,812, both filed Oct. 20, 2010.

TECHNICAL FIELD

Embodiments of the subject matter described herein relate generally to sensors and medical devices that utilize sensors. More particularly, embodiments of the subject matter relate to sensor assemblies configured to limit deflection of a beam having a sensing element disposed thereon.

BACKGROUND

Force sensors can be found in electronic devices and may be utilized for various applications. For example, infusion pump devices and systems are relatively well-known in the medical arts, for use in delivering or dispensing an agent, such as insulin or another prescribed medication, to a patient. Some infusion pump devices utilize a force sensor to detect an occlusion in a fluid path when administering the agent.

A typical infusion pump includes a pump drive system which typically includes a small motor and drive train components that convert rotational motor motion to a translational displacement of a stopper (or plunger) in a reservoir. The reservoir cooperates with tubing, a catheter and/or an infusion set to create a fluid path for carrying medication from the reservoir to the body of a user. Some fluid infusion devices include an occlusion detection feature that determines when an occlusion develops in the fluid path. Thus, medication infusion pump devices have included force sensors designed to detect and indicate a pump malfunction and/or non-delivery of the medication to the patient due to a fluid path occlusion. However, relatively small force sensors that provide relatively high sensitivity and/or accuracy over a narrow range of values (which may be necessary for occlusion detection) may be more susceptible to damage as a result of a physical impact or an applied force exceeding the intended measurement range.

BRIEF SUMMARY

An embodiment of a sensor assembly is provided. The sensor assembly includes a beam and a sensing element disposed on the beam. The sensor assembly also includes a structure configured to prevent deflection of the beam when a force applied to the sensor assembly is greater than a threshold value.

Also provided is an embodiment of a portable medical device. The portable medical device includes a sliding member and a drive system to displace the sliding member in a first direction. A sensor assembly is coupled to the drive system to measure force provided by the drive system to displace the sliding member in the first direction. The sensor assembly comprises a beam and a sensing element disposed on the beam. A back plate is coupled to the beam structure to inhibit deflection of the beam when a force applied to the sensor assembly is greater than a threshold value.

Another embodiment of a sensor assembly is also provided. This embodiment of the sensor assembly comprises a first structure comprising a rigid material and a second structure mechanically coupled to the first structure. The second structure comprises a deflectable portion, wherein the first structure limits deflection of the deflectable portion of the second structure towards the first structure in response to a force applied to the sensor assembly. The sensor assembly also includes a sensing element disposed on the deflectable portion.

In yet another embodiment, a sensor assembly comprises a beam structure comprising a plurality of beams, each beam having a sensing element disposed thereon, a loading element mechanically coupled to the plurality of beams, and a structure to prevent deflection of one or more beams of the plurality of beams when a force applied by the loading element in the direction of the structure is greater than a threshold value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
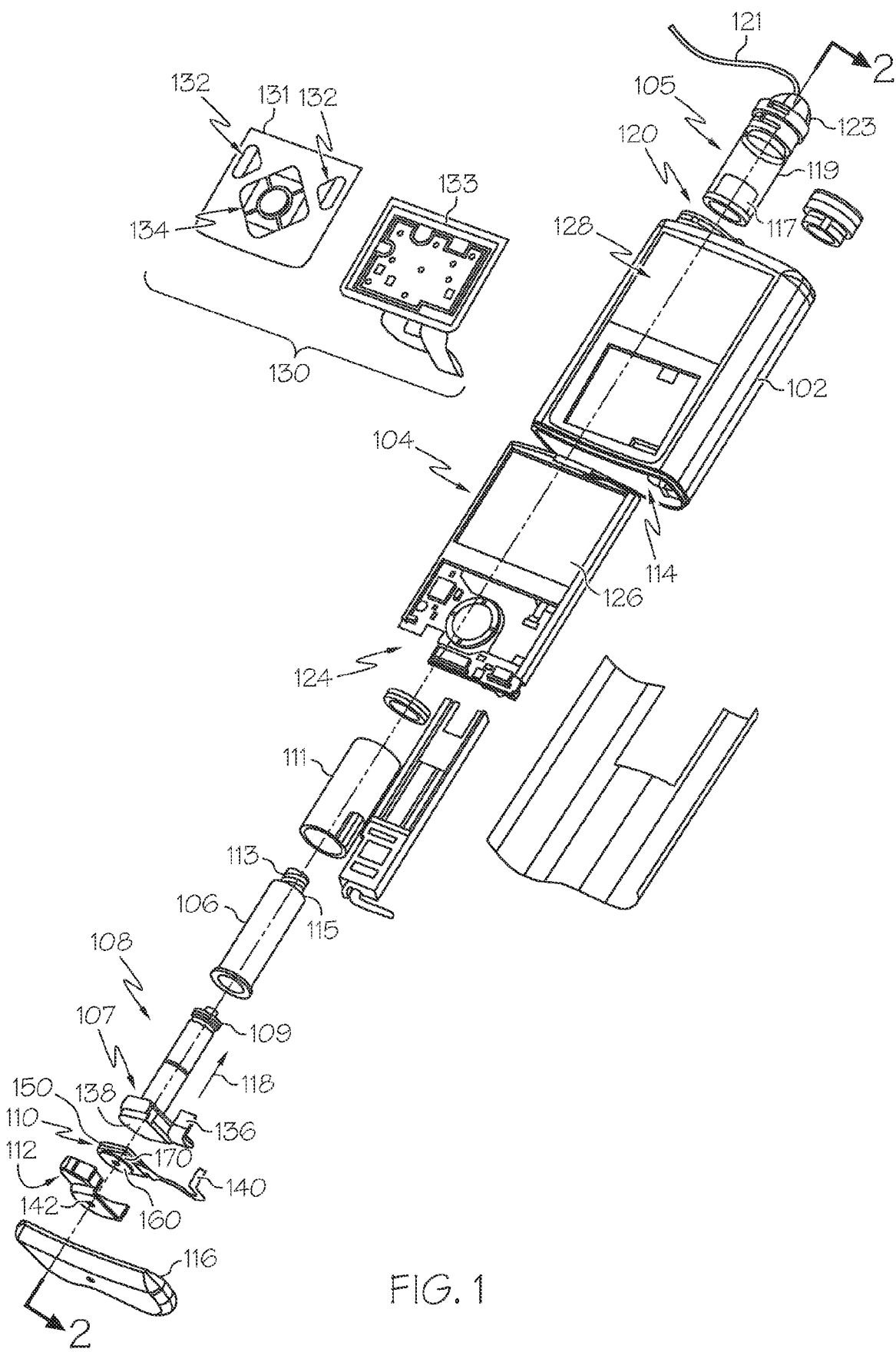
FIG. 1 is an exploded perspective view of an exemplary embodiment of an infusion pump.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The following description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the following description for the purpose of reference only, and thus are not intended to be limiting. For example, terms such as "upper", "lower", "above", and "below" might refer to directions in the drawings to which reference is made. Such terminology may include the words specifically mentioned above, derivatives thereof, and words of similar import. Similarly, the terms "first", "second", and other such numerical terms referring to structures do not imply a sequence or order unless clearly indicated by the context.

The technologies described below can be implemented in any electronic device having one or more sensors incorporated therein. Although the subject matter is applicable to any electronic device where it may be desirable to utilize the sensor assemblies described herein, the exemplary embodiments are implemented in the form of medical devices, such as portable electronic medical devices. Although many different applications are possible, the following description focuses on an infusion pump as part of an infusion system deployment. For the sake of brevity, conventional techniques related to infusion system operation, insulin pump and/or infusion set operation, force sensor design and operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893 which are herein incorporated by reference.

Figure 2:
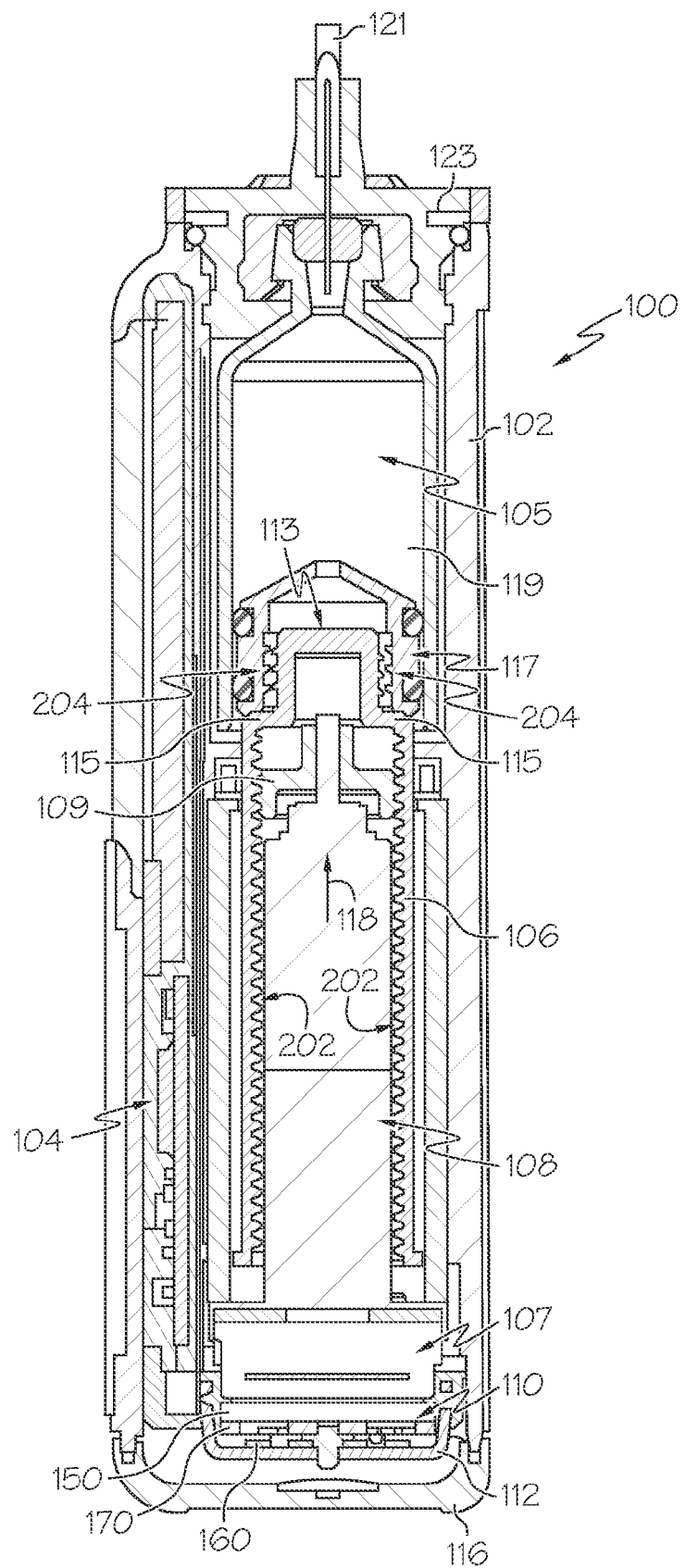
FIG. 2 is a cross-sectional view of the infusion pump as viewed along line 2-2 in FIG. 1 when assembled with a reservoir inserted in the infusion pump of FIG. 1.

FIGS. 1-2 depict an exemplary embodiment of an infusion pump 100. The infusion pump 100 is designed as a portable medical device suitable for infusing fluid into the body of a user, and in practice, may be carried or worn by the user. The infusion pump 100 may be configured to be interoperable with an infusion set as part of an insulin infusion system. The components of an insulin infusion system may be realized using different platforms, designs, and configurations, and the embodiment shown in FIG. 1 is not exhaustive or limiting. Moreover, as mentioned previously, other devices in an infusion system, other medical devices designed to address other patient needs, and other portable electronic devices could utilize a sensor assembly having the characteristics described herein.

The illustrated embodiment of infusion pump 100 includes, without limitation, a housing 102, an electronics assembly 104, a sliding member (or slide) 106, a drive system 108, a sensor assembly 110, and a capping member 112. The housing 102 includes an opening 120 adapted to receive a fluid-containing reservoir 105. FIG. 2 illustrates a cross-sectional view of the infusion pump 100 that illustrates the relationship between the drive system 108, the slide 106, the reservoir 105, and the sensor assembly 110 when assembled with the reservoir 105 inserted in the housing 102. It should be appreciated that FIGS. 1-2 depict the infusion pump 100 in a simplified manner; in practice, the infusion pump 100 could include additional elements, features, or components that are not shown or described in detail here.

The housing 102 is formed from a substantially rigid material having a hollow interior 114 adapted to allow the electronics assembly 104, reservoir 105, slide 106, drive system 108, sensor assembly 110, and capping member 112 to be disposed therein and enclosed by bottom portion 116. In the illustrated embodiment, the opening 120, the slide 106, and the drive system 108 are coaxially aligned in an axial direction (indicated by arrow 118). As described in greater detail below, the drive system 108 facilitates displacement of the slide 106 in the axial direction 118 to dispense fluid from the reservoir 105 (after the reservoir 105 has been inserted into opening 120), wherein the sensor assembly 110 is configured to measure axial forces (e.g., forces aligned with the axial direction 118) exerted on the sensor assembly 110. In various embodiments, the sensor assembly 110 may be utilized to detect one or more of the following: an occlusion in a fluid path that slows, prevents, or otherwise degrades fluid delivery from the reservoir 105 to a user's body; when the reservoir 105 is empty; when the slide 106 is properly seated with the reservoir 105; when a fluid dose has been delivered; when the infusion pump 100 is subjected to shock or vibration; when the infusion pump 100 requires maintenance.

In the illustrated embodiment, the electronics assembly 104 includes control electronics 124 coupled to a display element 126. In an exemplary embodiment, the display 126 is realized as a liquid crystal display (LCD), however, in alternative embodiments, the display 126 may be realized using another suitable display element. The display 126 may be utilized to present various types of information or data to the user, such as, without limitation: the current glucose level of the patient; the time; a graph or chart of the patient's glucose level versus time; device status indicators; alert messages; visual alert indicators; etc. The housing 102 includes a transparent window portion 128 that is aligned with the display 126 to allow the display 126 to be viewed by the user when the electronics assembly 104 is disposed within the interior 114 of the housing 102.

The control electronics 124 generally represent the hardware, firmware, processing logic and/or software (or combinations thereof) configured to control operation of the drive system 108 in a manner that is influenced by signals measured by and/or received from the sensor assembly 110 that are indicative of the axial force imparted to the sensor assembly 110. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 124 includes one or more programmable controllers that may be programmed to control operation of the infusion pump 100.

As illustrated in FIG. 1, the infusion pump 100 also includes a human-machine interface (HMI) 130 (or user interface) that is integral with or otherwise coupled to the housing 102. In an exemplary embodiment, the HMI 130 comprises HMI elements, such as buttons 132 and a directional pad 134, that are formed on a graphic keypad overlay 131 that overlies a keypad assembly 133, which includes features corresponding to the buttons 132, directional pad 134 or other user interface items indicated by the graphic keypad overlay 131. When assembled, the keypad assembly 133 is coupled to the control electronics 124, thereby allowing the HMI elements 132, 134 to be manipulated by the user to interact with the control electronics 124 and control operation of the infusion pump 100, for example, to administer a bolus of insulin, to change therapy settings, to change user preferences, to select display features, to set or disable alarms and reminders, and the like. In this regard, the control electronics 124 maintains and/or provides information to the display 126 regarding program parameters, delivery profiles, pump operation, alarms, warnings, statuses, or the like, which may be adjusted using the HMI elements 132, 134. In various embodiments, the HMI elements 132, 134 may be realized as physical objects (e.g., buttons, knobs, joysticks, and the like) or virtual objects (e.g., using touch-sensing and/or proximity-sensing technologies). For example, in some embodiments, the display 126 may be realized as a touch screen or touch-sensitive display, and in such embodiments, the features and/or functionality of the HMI elements 132, 134 may be integrated into the display 126 and the HMI 130 may not be present. In some embodiments, the electronics assembly 104 may also include alert generating elements coupled to the control electronics 124 and suitably configured to generate one or more types of feedback, such as, without limitation: audible feedback; visual feedback; haptic (physical) feedback; or the like.

Depending on the embodiment, the fluid-containing reservoir 105 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. The reservoir 105 typically includes a reservoir barrel 119 that contains the fluid and is concentrically and/or coaxially aligned with the slide 106 (e.g., in the axial direction 118) when the reservoir 105 is inserted into the infusion pump 100. The end of the reservoir 105 proximate the opening 120 may include a suitably configured fitting 123 (or cap) that secures the reservoir 105 in the housing 102, and which prevents displacement of the reservoir 105 in the axial direction 118 with respect to the housing 102 after the reservoir 105 is inserted into the housing 102. In an exemplary embodiment, the fitting 123 and/or reservoir 105 is configured to facilitate a fluid path from the reservoir 105 to a user. In this regard, a portion of the fitting 123 may extend through the opening 120 of the housing 102 and mate with tubing 121, thereby establishing fluid communication from the interior of the reservoir 105 and into the tubing 121 in a conventional manner. The tubing 121 may extend to an infusion set, which provides a fluid path to/from the body of the user. The opposing end of the reservoir 105 proximate the slide 106 includes a stopper 117 (or plunger) positioned to push fluid from inside the barrel 119 of the reservoir 105 along a fluid path through tubing 121 to a user. The slide 106 is configured to mechanically couple or otherwise engage with the stopper 117, thereby becoming seated with the stopper 117 and/or reservoir 105. As described in greater detail below in the context of FIG. 2, fluid is forced from the reservoir 105 via tubing 121 as the drive system 108 is operated to displace the slide 106 in the axial direction 118 toward the opening 120 in the housing 102.

In an exemplary embodiment, the drive system 108 includes a motor assembly 107 and a drive screw 109. The motor assembly 107 generally represents a motor and associated drive train components that convert rotational motor motion to a translational displacement of the slide 106 in the axial direction 118, and thereby engaging and displacing the stopper 117 of the reservoir 105. In some embodiments, the motor assembly 107 may also be powered to translate the slide 106 in the opposing direction (e.g., the direction opposite direction 118) to retract and/or detach from the reservoir 105 to allow the reservoir 105 to be replaced. In an exemplary embodiment, the motor assembly 107 includes a brushless DC motor, however, in other embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 105.

As best shown in FIG. 2, the drive screw 109 mates with threads 202 internal to the slide 106. When the motor assembly 107 is powered, the drive screw 109 rotates, and the slide 106 is forced to translate in the axial direction 118. In an exemplary embodiment, the infusion pump 100 includes a sleeve 111 to prevent the slide 106 from rotating when the drive screw 109 of the drive system 108 rotates. Thus, rotation of the drive screw 109 causes the slide 106 to extend or retract relative to the drive motor assembly 107. When the fluid infusion device is assembled and operational, the slide 106 contacts the stopper 117 to engage the reservoir 105 and control delivery of fluid from the infusion pump 100. In an exemplary embodiment, the shoulder portion 115 of the slide 106 contacts or otherwise engages the stopper 117 to displace the stopper 117 in the axial direction 118. In alternative embodiments, the slide 106 may include a threaded tip 113 capable of being detachably engaged with internal threads 204 on the stopper 117 of the reservoir 105, as described in detail in U.S. Pat. Nos. 6,248,093 and 6,485,465, which are incorporated by reference herein.

As shown in FIG. 1, the drive system 108 includes one or more electrical leads 136 adapted to be electrically coupled to the electronics assembly 104 to establish communication between the control electronics 124 and the drive system 108. In response to command signals from the control electronics 124 that regulate the amount of power supplied to the motor from a power supply, the motor actuates the drive train components to displace the slide 106 to force fluid from the reservoir 105, along a fluid path (including tubing 121 and an infusion set), thereby administering doses of the fluid contained in the reservoir 105 into the user's body. Preferably, the power supply is one or more batteries contained within the housing 102. Alternatively, the power supply may be a solar panel, capacitor, AC or DC power supplied through a power cord, or the like. In some embodiments, the control electronics 124 may operate the motor of the drive system 108 in a stepwise manner, typically on an intermittent basis; to administer discrete precise doses of the fluid to the user according to programmed delivery profiles. In alternative embodiments, the control electronics 124 may operate the motor continuously.

In an exemplary embodiment, the sensor assembly 110 includes a back plate structure 150 and a loading element 160. The back plate structure 150 is preferably affixed, adhered, mounted, or otherwise mechanically coupled to the bottom surface 138 of the drive system 108. Alternatively, the back plate structure 150 could be mounted to a different component of the infusion pump 100, such as the housing 102, a support structure, or any feature such that the back plate structure 150 resides between the bottom surface 138 of the drive system 108 and the bottom portion 116. The loading element 160 is disposed between the capping member 112 and a beam structure 170. The capping member 112 is contoured to accommodate and conform to the bottom of the sensor assembly 110 and the drive system 108. The capping member 112 is affixed to the interior of the housing 102 and prevents displacement of the sensor assembly 110 in the direction opposite the direction of force provided by the drive system 108 (e.g., the direction opposite direction 118).

As best illustrated by FIG. 2, the sensor assembly 110 is positioned between the motor assembly 107 and secured by the capping member 112 which is configured to prevent displacement of the sensor assembly 110 in a downward direction opposite the direction of arrow 118. Thus, the sensor assembly 110 is subjected to a reactionary compressive force when the drive system 108 and/or motor assembly 107 is operated to displace the slide 106 in the axial direction 118 in opposition to the fluid pressure in the reservoir 105. For example, if an occlusion developed within the fluid path, blocking fluid delivery from the infusion pump 100 to the body of the user, the fluid pressure would increase as the slide 106 is forced forward in the axial direction 118 by the drive system 108. Each time the control electronics 124 commands power to be supplied to the drive system 108, the slide 106 is driven forward into the reservoir 105, therefore increasing the fluid pressure in the reservoir 105. The fluid pressure is exerted against the slide 106, forcing it to back out of the reservoir 105; however, the drive system 108 prevents the slide 106 from retracting and the capping member 112 prevents displacement of the sensor assembly 110, thereby transferring the resultant force to the sensor assembly 110. Thus, under normal operating conditions the compressive force applied to the sensor assembly 110 by the drive system 108 and/or capping member 112 is correlated with the fluid pressure in the reservoir 105. As shown, electrical leads 140 are adapted to electrically couple the sensing elements of the sensor assembly 110 to the electronics assembly 104 to establish communication to the control electronics 124, wherein the control electronics 124 are configured to measure, receive, or otherwise obtain electrical signals from the sensing elements of the sensor assembly 110 that are indicative of the force applied by the drive system 108 in the axial direction 118, as described in greater detail below.

First Embodiment

FIGS. 3-6 depict an exemplary embodiment of a sensor assembly 300 suitable for use as the sensor assembly 110 of FIG. 1. The illustrated embodiment of the sensor assembly 300 includes a back plate structure 350 (also referred to herein as a back plate 350), a loading structure 360 (also referred to herein as a loading element), and a beam structure 370 disposed between the back plate 350 and the loading element 360. The beam structure 370 includes one or more beams 302 mechanically coupled to the loading element 360, such that a compressive force applied to the loading element 360 towards the back plate 350 deflects the beams 302 towards the back plate 350 until the inner portion 318 of the beams 302 contact the back plate 350. Each beam 302 has a sensing element 304 disposed thereon, wherein an electrical characteristic of the sensing element 304 is influenced by the amount of deflection of the respective beam 302, and thus, is indicative of the force applied to the sensor assembly 300, as described in greater detail below.

The back plate 350 comprises a rigid plate-like structure. In this regard, the back plate 350 has a substantially planar surface 310 and is comprised of a rigid material, such as carbon, steel, or another suitable material.

Figure 4:
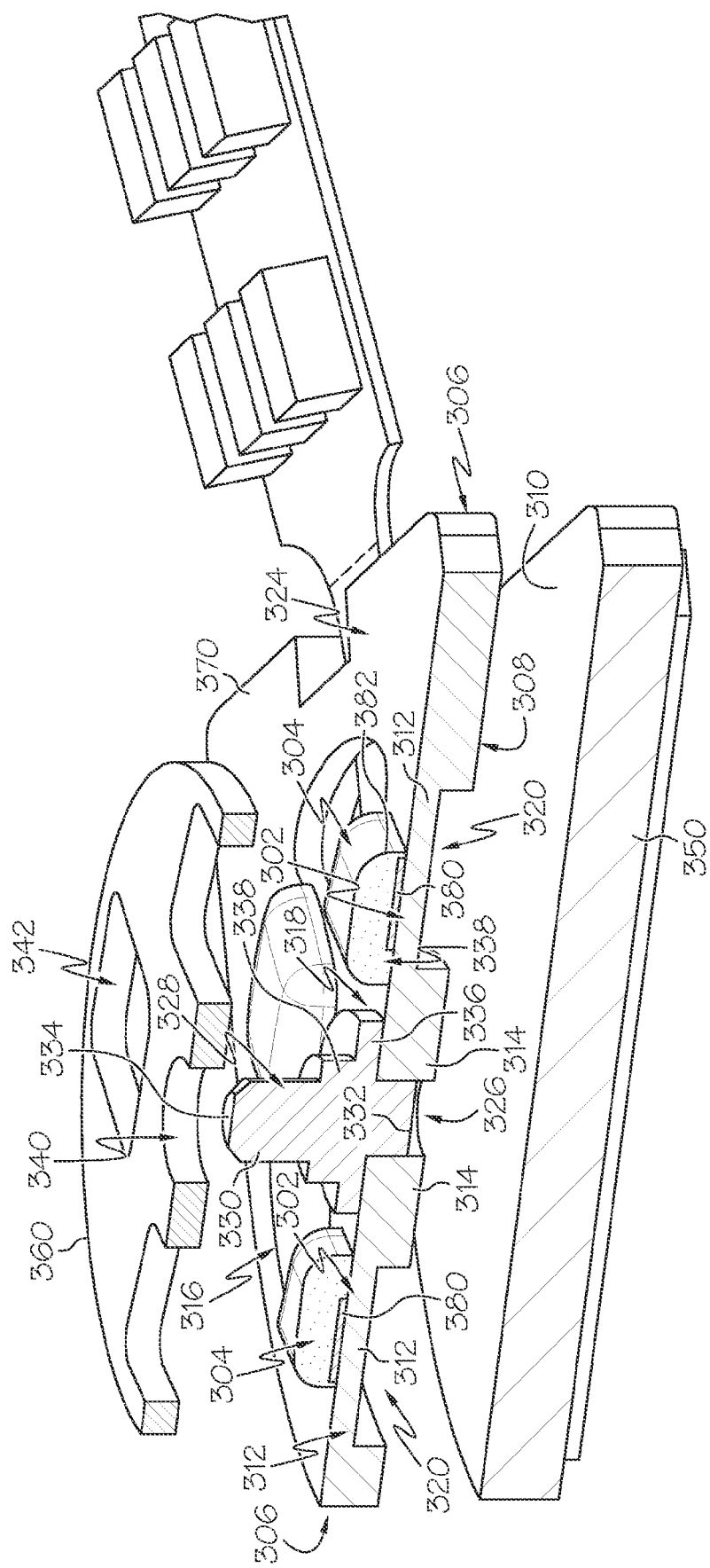
FIG. 4 is an exploded perspective view of the sensor assembly of FIG. 3 illustrating a partial cross-section of the sensor assembly as viewed along line 4-4 in FIG. 3.

In certain embodiments, the beam structure 370 is realized as a flexible metallic material, although in other embodiments, another deflectable material with desirable durability and aging characteristics may be used. As best shown in FIG. 4, an outer portion 306 of the beam structure 370 has a substantially planar surface 308 disposed adjacent to and in contact with the planar surface 310 of the back plate 350. The outer portion 306 of the beam structure 370 may be affixed, adhered, welded or otherwise mounted to the planar surface 310 about the periphery of the back plate 350. Thus, the outer portion 306 is supported by the back plate 350 and comprises a supported portion of the beam structure 370. In some embodiments, the outer portion 306 of the beam structure 370 may be integral with the back plate 350. In an exemplary embodiment, the outer portion 306 provides a substantially uniform thickness about the periphery of the beam structure 370. The thickness of the outer portion 306 of the beam structure 370 may vary depending on the needs of a particular embodiment.

Figure 5:
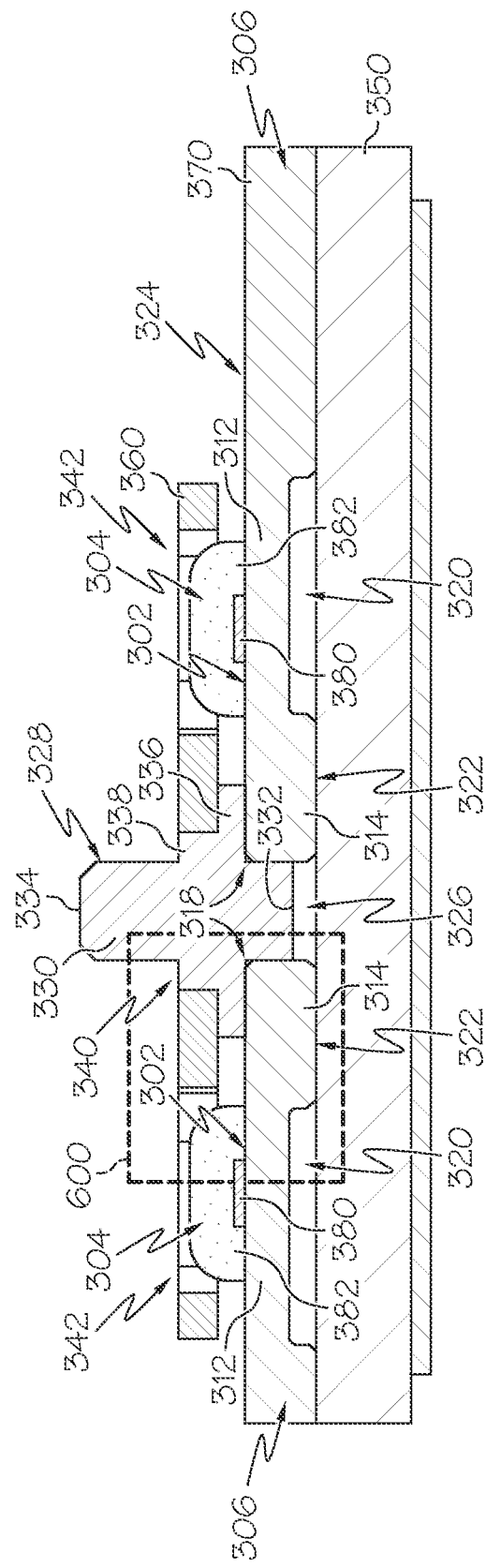
FIG. 5 is a cross-sectional view of the sensor assembly of FIG. 3 illustrating a cross-section as viewed along line 4-4 in FIG. 3.
Figure 6:
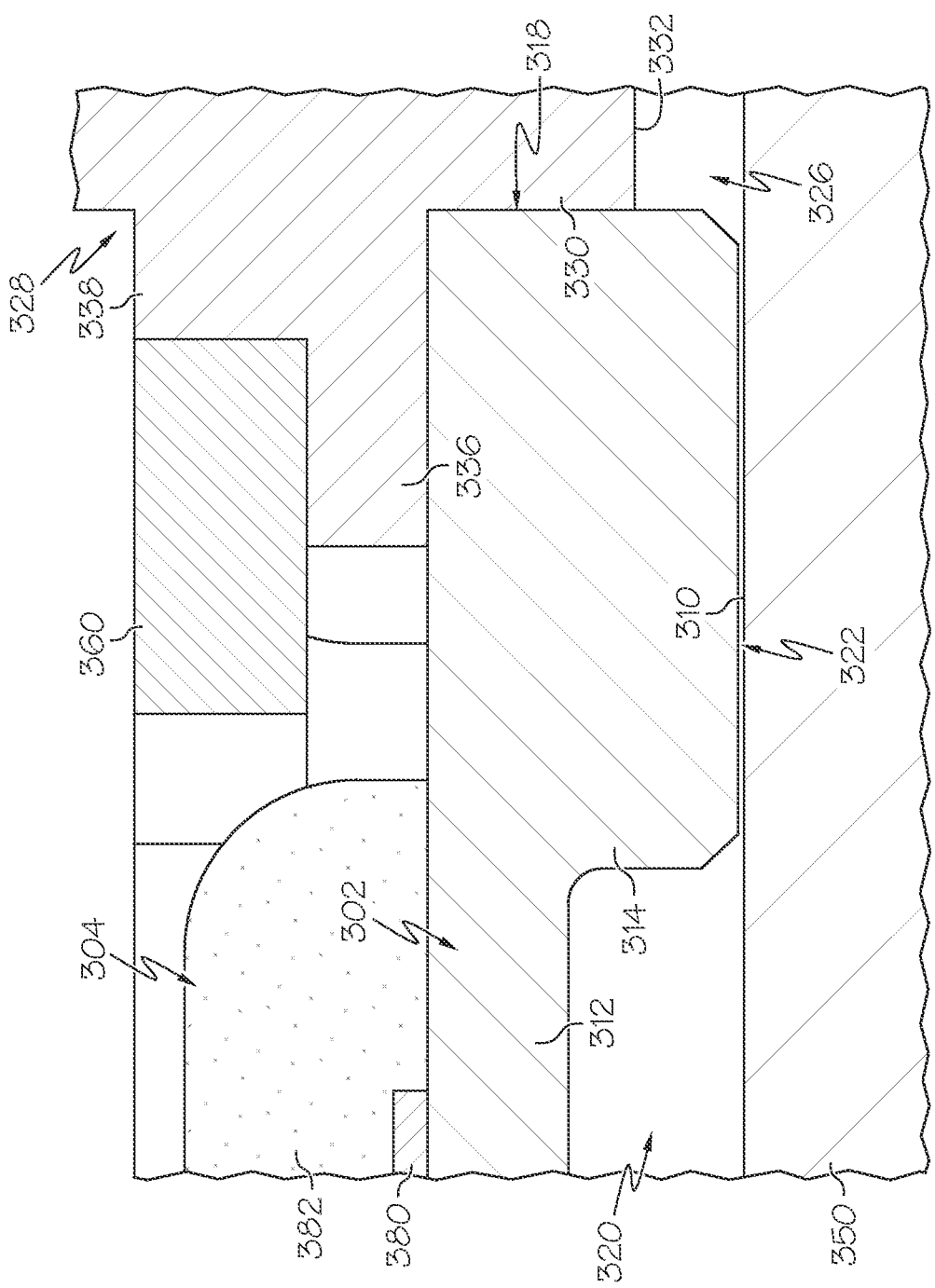
FIG. 6 is an enlarged cross-sectional view of a portion of the sensor assembly of FIGS. 3-5.

As best shown in FIGS. 4-5, each beam 302 comprises an arm portion 312 of the beam structure 370 that extends radially inward from the outer portion 306 to an end portion 314. Voided (or cutout) regions 316 are formed in the beam structure 370 adjacent to the arm portions 312 of the beams 302, such that the each voided region 316 physically separates arm portions 312 of adjacent beams 302. The arm portions 312 are configured to provide voided regions 320 between the beams 302 and the surface 310 of the back plate 350 such that the arm portions 312 are physically separated from the back plate 350. The end portions 314 of the beams 302 are configured such that in the absence of a compressive force applied to the back plate 350 and/or loading element 360, the end portions 314 do not contact the back plate 350. As best shown by the detailed view of region 600 in FIG. 6, the end portions 314 are configured to provide an airgap 322 separating the end portions 314 of the beams 302 from the surface 310 of the back plate 350. In this manner, the arm portions 312 and the end portions 314 are freestanding, detached, or otherwise separated from the back plate 350. The separation distance between the end portions 314 and the surface 310 of the back plate 350 provided by the airgap 322 is less than the separation distance between the arm portions 312 and the back plate 350 provided by the voided regions 320. In the illustrated embodiment, the end portions 314 of the beams 302 are integral and form an inner portion 318 of the beam structure 370. In one embodiment, the inner portion 318 is coaxially aligned with a drive system (e.g., drive system 108 in the axial direction 118).

Figure 3:
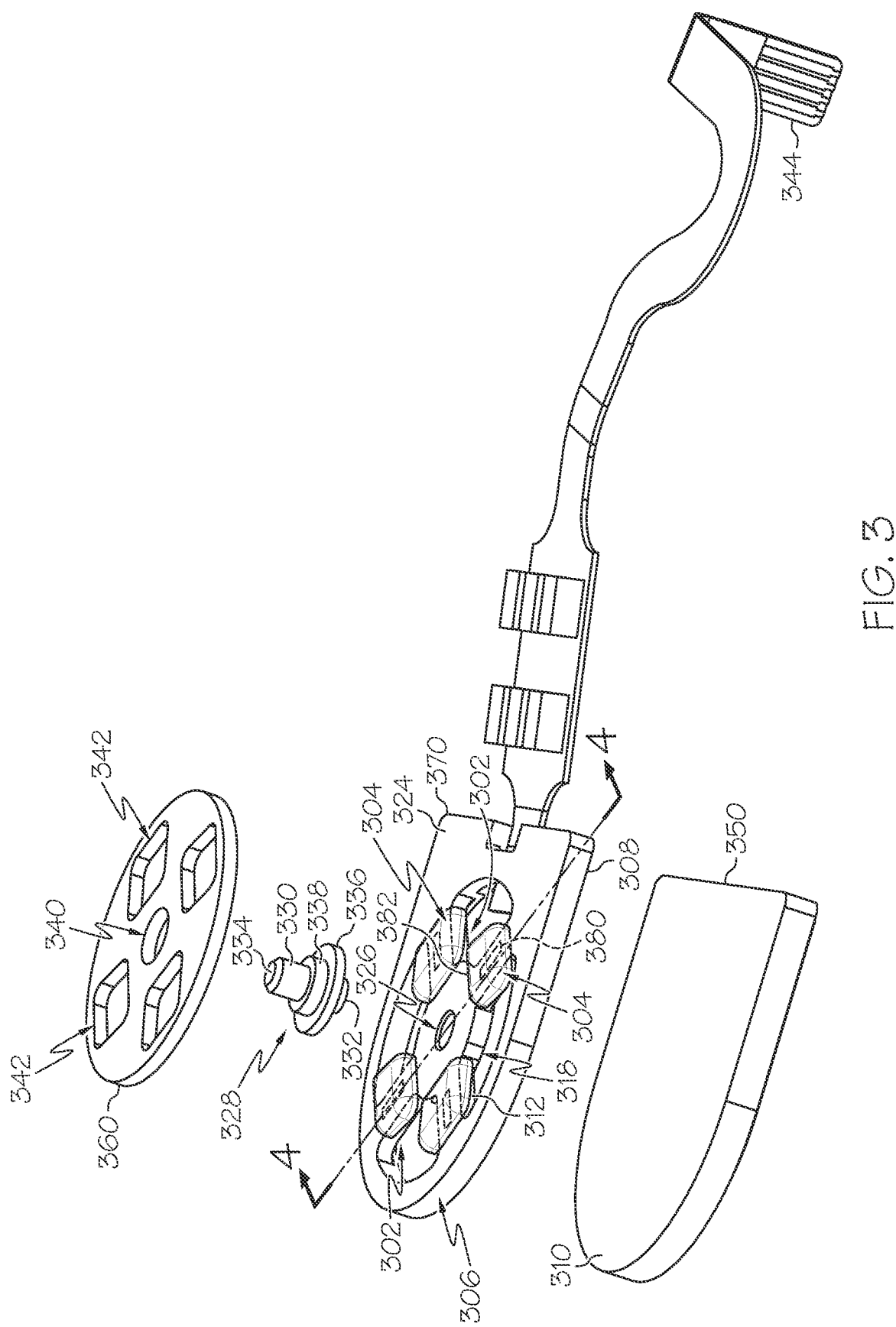
FIG. 3 is an exploded perspective view of an exemplary embodiment of a sensor assembly suitable for use with the infusion pump of FIG. 1.

As best shown in FIGS. 3-5, the inner portion 318 includes a circular opening 326 formed in the center of the inner portion 318 and adapted to receive a dowel member 328 that mechanically couples the beams 302 to the loading element 360. In the illustrated embodiment, the dowel member 328 includes a cylindrical portion 330 having a circumference that is less than the circumference of the opening 326 such that an end 332 of the cylindrical portion 330 is capable of being inserted into the opening 326. An opposing end 334 of the cylindrical portion 330 protrudes through an opening in the loading element 360 to align the sensor assembly 300 with an opening in a capping member (e.g., capping member 112), as described in greater detail below. In an exemplary embodiment, the dowel member 328 includes an outer circular rim portion 336 having a circumference that is greater than the circumference of the opening 326, such that the rim portion 336 overlaps the inner portion 318 of the beam structure 370 and prevents displacement of the dowel member 328 towards the back plate 350 with respect to the beam structure 370. Thus, the rim portion 336 distributes a compressive force applied to the sensor assembly 300 across the beams 302 in a substantially even manner. In some embodiments, the rim portion 336 is affixed, adhered, welded, or otherwise mounted to the inner portion 318 such that the dowel member 328 is fixed with respect to the inner portion 318 of the beam structure 370. In the illustrated embodiment, the outer circumference of the rim portion 336 is less than the outer circumference of the inner portion 318 of the beam structure 370, such that the rim portion 336 does not overlap or otherwise contact the arm portions 312 of the beams 302, however, in other embodiments, the outer circumference of the rim portion 336 may be greater than the outer circumference of the inner portion 318 and overlap at least some of the arm portions 312 of the beams 302. The length of the portion of the cylindrical portion 330 that extends from the outer circular rim portion 336 to the end 332 proximate the back plate 350 is less than the thickness of the end portions 314, such that the end 332 of the dowel member 328 does not contact the surface 310 of the back plate 350 before the end portions 314 contact the back plate 350. The dowel member 328 also includes an inner circular rim portion 338 having a circumference that is greater than the circumference of the cylindrical portion 330 but less than the circumference of the outer circular rim portion 338 for seating the loading element 360, as described below.

As best shown in FIGS. 3-5, the arm portion 312 of each beam 302 has a sensing element 304 disposed thereon. In an exemplary embodiment, each sensing element 304 is realized as a strain-sensitive element 380, such as a strain gauge, wherein deflection of the beam 302 produces a strain and corresponding change in an electrical characteristic of the strain-sensitive element. For example, a strain-sensitive element 380 may be realized as a serpentine wire or another patterned conductor rigidly joined to a surface of a beam 302, such that deflection of the beam 302 produces a strain and corresponding change in the resistance of the wire. In an exemplary embodiment, each strain-sensitive element 380 is realized as a patterned conductor printed on a substrate that is affixed to the surface 324 of the arm portion 312 of the respective beam 302, that is, the surface of the arm portions 312 opposite the surface 308 of the beam structure 370 that is affixed to the back plate 350. The strain-sensitive elements 380 may be adhered to the beams 302 by applying a glass coating that adheres the substrate to the beams 302. In an exemplary embodiment, a gel coating 382 (illustrated as being transparent in FIG. 3) is applied to the strain-sensitive elements 380 to prevent oxidation of the glass coating that adheres the strain-sensitive elements 380 to the beams 302. The gel coating 382 may also act as a dampener during an overload condition (e.g., in response to the infusion pump 100 being dropped or shaken) to prevent applied forces exceeding the intended measurement range of the sensor assembly 300 from being transferred directly to the strain-sensitive elements 380. Because the strain-sensitive elements 380 are rigidly affixed to the arm portions 312, deflection exhibited by the arm portions 312 is directly transferred to the strain-sensitive elements 380. Electrical leads 344 are electrically coupled to the strain-sensitive elements 380 and electrically couple the strain-sensitive elements 380 to control electronics (e.g., control electronics 124) configured to obtain or otherwise receive electrical signals from the strain-sensitive elements 380 that are indicative of the amount of force applied to sensor assembly 300, as described in greater detail below. In an exemplary embodiment, the strain-sensitive elements 380 are electrically configured to provide a Wheatstone bridge circuit that is utilized to determine the force applied to the sensor assembly 300 based on the resistances of strain-sensitive elements 380.

In the illustrated embodiment, the loading element 360 is realized as a circular disc-like structure having an outer circumference that is less than the inner circumference of the outer portion 306 of the beam structure 370 to prevent the loading element 360 from contacting the outer portion 306 of the beam structure 370 when the beams 302 are deflected towards the back plate 350. Accordingly, for convenience, the loading element 360 may alternatively be referred to herein as a loading disc. As best shown in FIG. 3, in an exemplary embodiment, the loading disc 360 includes a circular opening 340 disposed at the center of the loading disc 360 to align the loading disc 360 with the dowel member 328. The circumference of the opening 340 is greater than the circumference of the inner circular rim portion 338 but less than the circumference of the outer circular rim portion 336 to allow the loading disc 360 to be seated on the dowel member 328. In this manner, the outer circular rim portion 338 mechanically couples but physically separates the loading disc 360 and the end portions 314 and/or inner portion 318 of the beam structure 370, as shown by FIG. 5. In an exemplary embodiment, the opening 340 in the loading disc 360 is configured to be flush with the inner rim portion 338 to limit, prevent, or otherwise restrict radial displacement of the loading disc 360 with respect to the dowel member 328 in a drop or shock condition. The loading disc 360 includes a plurality of voided (or cutout) regions 342 aligned with the sensing elements 304 and configured such that the loading disc 360 does not contact the sensing elements 304. The loading disc 360 comprises a rigid material that does not substantially compress under the range of forces to be measured by the sensor assembly 300. The loading disc 360 is subjected to forces that exceed the intended measurement range for the sensor assembly 300, as described below. The thickness of the loading disc 360 is chosen to be as thin as possible while retaining sufficient rigidity to ensure that compressive forces applied to the sensor assembly 300 are transferred to the inner portion 318 of the beams 302.

By virtue of the separation between the beams 302 and the back plate 350, the beams 302 form deflectable portions of the beam structure 370 that exhibit deflection in response to compressive forces applied to the sensor assembly 300. The beams 302 are configured such that the end portions 314 of the beams 302 contact the surface 310 of the back plate 350 when a compressive force applied to the sensor assembly 300 is greater than a threshold value, thereby limiting, preventing, or otherwise inhibiting additional deflection of the arm portions 312 of the beams 302. In this regard, the separation distance provided by the airgap 322 and the flexion of the arm portions 312 are calibrated or otherwise configured to establish an upper limit on the compressive force that the beams 302 are subjected to. The threshold value is chosen to be greater than or equal to the upper end of the intended measurement range for the sensor assembly 300. In this manner, the threshold value is indicative of an overload condition, that is, an event that would result in the sensor assembly 300 being subjected to compressive forces exceeding the intended measurement range, for example, in the event a device including the sensor assembly 300 (e.g., infusion pump 100) is dropped. Thus, the threshold value corresponds to an upper limit on the amount of deflection that the beams 302 and/or sensing elements 304 are subjected to and protects the sensing elements 304 and the beams 302 from compressive forces exceeding the intended measurement range.

When the compressive force applied to the sensor assembly 300 is less than the threshold value, the beams 302 are freely movable (or deflectable) with respect to the back plate 350 and the back plate 350 does not influence the deflection of the beams 302. A compressive force applied to the sensor assembly 300 that is less than the threshold value causes deflection of the arm portions 312 of the beams 302, thereby reducing the separation distance between the end portions 314 and the surface 310 of the back plate 350 (e.g., reducing the size of the airgap 322) and producing a corresponding change in the electrical characteristic of the sensing elements 304. A force applied to the sensor assembly 300 that is equal to the threshold value causes the end portions 314 to contact the surface 310 of the back plate 350, wherein the rigid material of the back plate 350 provides support and prevents further displacement of the end portions 314 towards the back plate 350. Thus, the deflection of the arm portions 312 does not increase in response to additional force applied to the sensor assembly 300 and is limited to an amount corresponding to the separation distance of the airgap 322. Any additional compressive force applied to the sensor assembly 300 is distributed across the back plate 350, the loading disc 360, the end portions 314 and/or the outer portion 306 of the beam structure 370, thereby limiting, preventing, or otherwise inhibiting additional deflection of the arm portions 312.

In accordance with one or more embodiments, the sensor assembly 300 is intended to measure forces between 0 pounds (0 N) and 5.0 pounds (22.2 N) with the desired resolution of less than or equal to 0.01 pounds (0.04 N). The threshold value for a compressive force that achieves sufficient deflection of the beams 302 such that the end portions 314 contact the surface 310 of the back plate 350 may be chosen to be a force value greater than the upper end of the intended measurement range that is sufficiently likely to compromise the structural integrity of the beams 302 and/or arm portions 312, strain gauges 380, the beam structure 370, and/or another member of the sensor assembly 300. For example, the threshold value for a compressive force may be chosen to be about one hundred percent to about two hundred percent of the upper end of the intended measurement range. In one embodiment, where the intended measurement range for the sensor is between 0 pounds (0 N) and 5.0 (22.2 N) pounds of force with the desired resolution of less than or equal to 0.01 pounds (0.04 N), and the beams 302 and/or airgaps 322 are calibrated to provide a threshold force value of about 7.0 pounds (31.1 N).

Referring again to FIGS. 1-2, and with continued reference to FIGS. 3-6, in an exemplary embodiment, sensor assembly 110 is realized as the sensor assembly 300 of FIG. 3. As shown in FIG. 1, the capping member 112 includes an opening 142 adapted to allow the end 334 of the dowel member 328 that protrudes through the loading disc 360 to be inserted into the capping member 112. Thus, the capping member 112 prevents lateral displacement of the dowel member 328, which in turn, limits, prevents, or otherwise restricts lateral displacement of the sensor assembly 300 with respect to the capping member 112. In accordance with one or more embodiments, the thickness of the loading disc 360 and the inner rim portion 338 are substantially equal to provide a continuous surface, such that the capping member 112 simultaneously contacts the loading disc 360 and the inner rim portion 338. In an exemplary embodiment, the opening 142 in the capping member 112, the opening 340 in the loading disc 360, the cylindrical portion 330 of the dowel member 328, and the circular opening 326 in the inner portion 318 of the beam structure 370 are concentrically aligned in the axial direction 118.

Depending on the embodiment, the back plate 350 may be affixed, adhered, mounted, or otherwise mechanically coupled to the bottom surface 138 of the drive system 108. When the drive system 108 drives the slide 106 forward into the reservoir 105 in the axial direction 118, fluid pressure increases, producing a reactionary force on the drive system 108 in the opposite direction which is transferred to the back plate 350. The capping member 112 prevents displacement of the sensor assembly 300 and effectively maintains the loading disc 360 and/or dowel member 328 in a fixed position with respect to the capping member 112 and/or housing 102. As a result, the reactionary force is transferred to the beams 302 by the loading disc 360 and/or rim portion 336 of the dowel member 328. In this manner, the capping member 112 is configured to deflect the beams 302 towards the surface 310 of the back plate 350 in response to the force provided by the drive system 108 in the axial direction 118. The deflection of the beams 302 is correlated with the axial force applied to the sensor assembly 300 and produces a corresponding increase in the strain exerted upon sensing elements 304. Thus, when the sensing elements 304 are each realized as strain-sensitive elements such as strain gauges, the resistance of the strain-sensitive elements 380 corresponds to or is otherwise correlated with the force applied by the drive system 108, which in turn corresponds to or is otherwise correlated with the fluid pressure in the reservoir 105.

The control electronics 124 are electrically coupled to the strain-sensitive elements 380 and configured to measure, receive, or otherwise obtain electrical signals from the strain-sensitive elements 380 that correspond to the resistance of the strain-sensitive elements 380. For example, the control electronics 124 may regulate the supply of an injection signal (e.g., a constant voltage or constant current) from a power supply for the infusion pump 100 to the strain-sensitive elements 380 and measure or otherwise obtain response signal (e.g., a measured current or voltage) caused by the injection signal, wherein the response signal is influenced by the resistance of the strain-sensitive elements 380 and therefore correlated with the fluid pressure of the reservoir 105 and/or force applied by the drive system 108 in the axial direction 118. For example, injecting a constant current signal will result in a measured voltage signal across the strain-sensitive elements 380 which is directly related to the resistance of the strain-sensitive elements 380, and therefore, is also directly related to the fluid pressure of the reservoir 105 and/or force applied by the drive system 108 in the axial direction 118. Conversely, injecting a constant voltage signal will result in a measured current signal through the strain-sensitive elements 380 which is inversely related to the resistance of the strain-sensitive elements 380, and therefore, is also inversely related to the fluid pressure of the reservoir 105 and/or force applied by the drive system 108 in the axial direction 118.

The control electronics 124 may utilize the relationship between the injection signal and the response signal to calculate, determine, or otherwise obtain values corresponding to the electrical characteristic of the sensing elements 304 that are influenced by the deflection of the beams 302. In this manner, the control electronics 124 may calculate or otherwise determine the force provided or otherwise applied by the drive system 108 in the axial direction 118 based upon the relationship between the injection signal the response signal. In some embodiments, the control electronics 124 may also calculate or otherwise determine the fluid pressure in the reservoir 105 based upon the force provided by the drive system 108 to displace the slide 106.

As set forth above, the control electronics 124 may be configured to modify or otherwise regulate the power provided to the drive system 108 and/or perform additional functions, operations, tasks, processes, and the like based upon the signals obtained from the sensor assembly 300. For example, in various embodiments, based upon the signals obtained from the sensor assembly 300, the control electronics 124 may be configured to perform one or more of the following: detect an occlusion in the fluid path from the reservoir 105 and/or infusion pump 100 to a user; detect when the slide 106 is properly seated with a stopper of the reservoir 105; detect the removal of one or more components in the fluid path such as disconnecting the infusion set, disconnecting the tubing, or the like; detect when the reservoir 105 is empty. Examples of actions that may be undertaken by the control electronics 124 are described in greater detail in U.S. Pat. No. 6,485,465, which is incorporated by reference herein.

Second Embodiment

Figure 7:
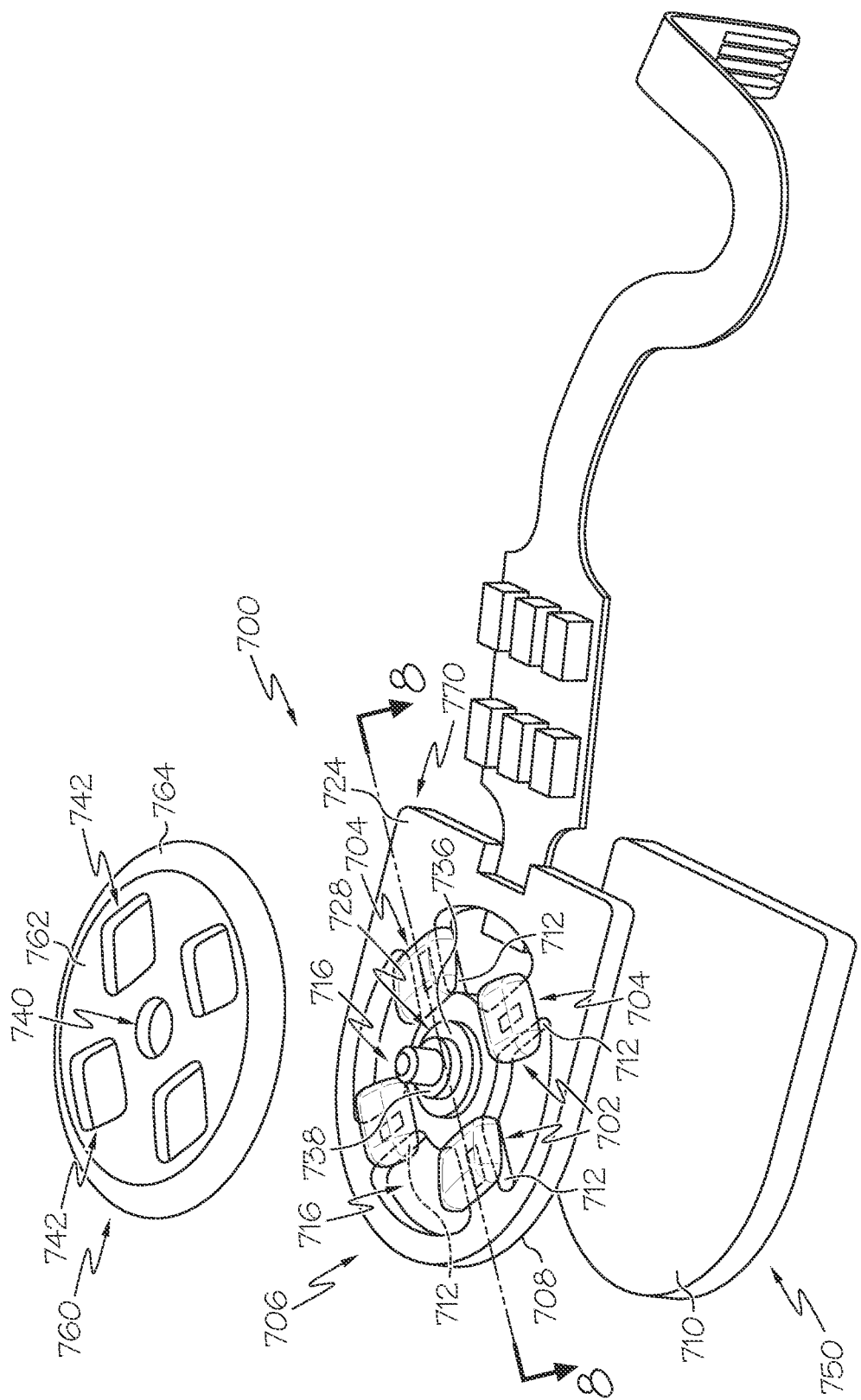
FIG. 7 is a perspective view of an another embodiment of a sensor assembly suitable for use with the infusion pump of FIG. 1.
Figure 8:
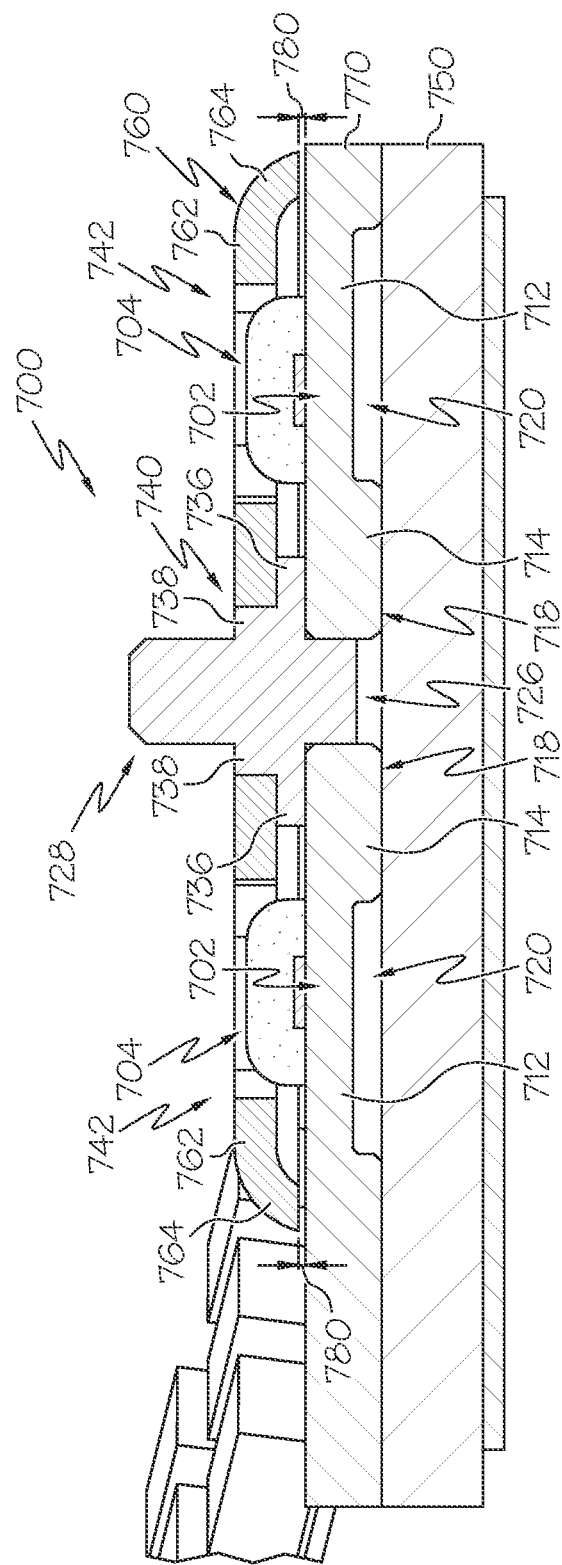
FIG. 8 is a cross-sectional view of the sensor assembly of FIG. 7 illustrating a cross-section as viewed along line 8-8 in FIG. 7.

FIGS. 7-8 depict another exemplary embodiment of a sensor assembly 700 suitable for use as the sensor assembly 110 of FIG. 1. The illustrated embodiment of the sensor assembly 700 includes a loading structure 760 (also referred to herein as a loading element), a back plate structure 750 (or back plate), and a beam structure 770 disposed between the back plate 750 and the loading element 760. Various elements of sensor assembly 700 are similar to counterpart elements described above in the context of sensor assembly 300 of FIGS. 3-6, and the common features of such elements will not be redundantly described here in the context of FIGS. 7-8. As described above in the context of FIGS. 3-6, the beam structure 770 includes one or more beams 702 mechanically coupled to the loading element 760, such that a compressive force applied to the loading element 760 towards the back plate 750 deflects the beams 702 towards the back plate 750. Each beam 702 has a sensing element 704 disposed thereon, wherein an electrical characteristic of the sensing element 704 is influenced by the amount of deflection of the respective beam 702, and thus, is indicative of the force applied to the sensor assembly 700. As described in greater detail below, the loading element 760 includes a feature 764 that prevents, inhibits, or otherwise limits deflection of the beams 702 when the compressive force applied to the sensor assembly 700 exceeds the intended measurement range for the sensor assembly 700.

As illustrated in FIGS. 7-8, the substantially planar surface 708 of the outer portion 706 of the beam structure 770 is disposed adjacent to and in contact with the planar surface 710 of the back plate 750, and the outer portion 706 may be affixed, adhered, welded or otherwise mounted to the planar surface 710 about the periphery of the back plate 750 to provide a supported portion of the beam structure 770 in a similar manner as described above in the context of FIGS. 3-6. Each beam 702 comprises an arm portion 712 of the beam structure 770 that extends radially inward from the supported outer portion 706 to an end portion 714. Voided regions 716 physically separate arm portions 712 of adjacent beams 702, and the arm portions 712 are configured to provide voided regions 720 between the beams 702 and the surface 710 of the back plate 750 such that the arm portions 712 are physically separated from the back plate 750. In the absence of a compressive force applied to the back plate 750 and/or loading element 760, the end portions 714 of the beams 702 do not contact the back plate 750 and the beams 702 are freestanding, detached, or otherwise separated from the back plate 750. In the illustrated embodiment, the end portions 714 of the beams 702 are integral to form an inner portion 718 of the beam structure 770 that is coaxially aligned with a drive system (e.g., drive system 108 in the axial direction 118). The inner portion 718 includes a circular opening 726 formed in the center of the inner portion and adapted to receive a dowel member 728 that mechanically couples the beams 702 to the loading element 760. A rim portion 736 of the dowel member 728 has a circumference that is greater than the circumference of the opening 726, such that the rim portion 736 overlaps the inner portion 718 of the beam structure 770 to prevent displacement of the dowel member 728 and/or loading element 760 towards the back plate 750 with respect to the inner portion 718 and distribute a compressive force applied to the sensor assembly 700 across the beams 702 in a substantially even manner.

Still referring to FIGS. 7-8, in an exemplary embodiment, the loading element 760 includes an inner planar portion 762 having a portion 764 that extends from the inner planar portion 762. In an exemplary embodiment, the extension portion 764 is realized as a curved or rounded portion about the periphery of the inner portion 762 that is curved or rounded towards the beam structure 770. In the illustrated embodiment, the inner portion 762 is realized as a circular disc-like structure having the rounded portion 764 circumscribing its perimeter. In this manner, the rounded portion 764 provides a curved rim about the periphery of the inner portion 762. For convenience, the loading element 760 may alternatively be referred to herein as a domed loading disc and the rounded or curved portion 764 of the disc-like structure 762 may alternatively be referred to herein as a shoulder portion. The loading disc 760 comprises a rigid material that does not substantially compress under the range of forces to be measured by the sensor assembly 700.

In a similar manner as described above, the domed loading disc 760 includes a circular opening 740 disposed at the center of the domed loading disc 760 to allow the loading disc 760 to be seated on the dowel member 728. In this manner, the substantially rigid rim portion 736 mechanically couples but physically separates the inner planar portion 762 of the domed loading disc 760 and the end portions 714 and/or inner portion 718, as best illustrated by FIG. 8. In an exemplary embodiment, the opening 740 in the loading disc 760 is configured to be flush with the dowel member 728 to limit, prevent, or otherwise restrict radial displacement of the domed loading disc 760 with respect to the dowel member 728. The domed loading disc 760 also includes a plurality of voided (or cutout) regions 742 aligned with the sensing elements 704 and configured such that the loading disc 760 does not contact the sensing elements 704.

As best illustrated in FIG. 8, the outer circumference of the domed loading disc 760 is greater than the inner circumference of the outer portion 706 of the beam structure 770 such that the shoulder portion 764 overlaps the outer portion 706 and is capable of contacting the outer portion 706 when the beams 702 are deflected towards the back plate 750. In an exemplary embodiment, the shoulder portion 764 of the domed loading disc 760 and the thickness of the rim portion 736 are configured to provide an airgap 780 separating the shoulder portion 764 from the surface 724 of the outer portion 706 of the beam structure 770.

By virtue of the separation between the beams 702 and the back plate 750, the beams 702 form deflectable portions of the beam structure 770 that exhibit deflection in response to compressive forces applied to the sensor assembly 700 that displace the inner portion 718 with respect to the supported outer portion 706. In an exemplary embodiment, the airgap 780 is configured such that the shoulder portion 764 of the domed loading disc 760 contacts the surface 724 of the outer portion 706 of the beam structure 770 when a compressive force applied to the sensor assembly 700 is greater than a threshold value. In this regard, the separation distance provided by the airgap 780 is calibrated or otherwise configured to establish an upper limit on the compressive force that the arm portions 712 of the beams 702 are subjected to. In an exemplary embodiment, the threshold value is chosen to be greater than or equal to the upper end of the intended measurement range for the sensor assembly 700. In this manner, the threshold value is indicative of an overload condition, that is, an event that would result in the sensor assembly 700 being subjected to compressive forces exceeding the intended measurement range, for example, in the event a device including the sensor assembly 700 (e.g., infusion pump 100) is dropped.

Due to the rigidity of the domed loading disc 760, when the shoulder portion 764 is in contact with the outer portion 706 of the beam structure 770, additional displacement of the inner portion 718 and/or end portions 714 towards the back plate 750 with respect to the outer portion 706 is inhibited, restricted or otherwise prevented. In this manner, the shoulder portion 764 of the domed loading disc 760 limits, prevents, or otherwise inhibits additional deflection of the arm portions 712 of the beams 702. Thus, the threshold value corresponds to an upper limit on the amount of deflection that the beams 702 and/or sensing elements 704 are subjected to and protects the sensing elements 704 and the beams 702 from compressive forces exceeding the intended measurement range. Additional compressive forces applied to the sensor assembly 700 exceeding the threshold value are transferred to the domed loading disc 760 and the outer portion 706 of the beam structure 770 and away from the beams 702. In this manner, the loading disc 760, the outer portion 706 of the beam structure 770 and/or the back plate 750 are subjected to forces that exceed the intended measurement range for the sensor assembly 700.

In a similar manner as described above, when the compressive force applied to the sensor assembly 700 is less than the threshold value, the beams 702 are freely movable (or deflectable) and the domed loading disc 760 does not influence the deflection of the beams 702. A compressive force applied to the sensor assembly 700 that is less than the threshold value causes deflection of the arm portions 712 of the beams 702, thereby reducing the separation distance between the shoulder portion 764 and the surface 724 of the outer portion 706 (e.g., reducing the size of the airgap 780) and producing a corresponding change in the electrical characteristic of the sensing elements 704. A force applied to the sensor assembly 700 that is equal to the threshold value causes the shoulder portions 764 to contact the surface 724 of the outer portion 706 of the beam structure 770, wherein the rigid material of the domed loading disc 760 provides support and prevents further displacement of the end portions 714 of the beams 702. Thus, the deflection of the arm portions 712 does not increase in response to additional force applied to the sensor assembly 700 and is limited to an amount corresponding to the separation distance of the airgap 780. Any additional compressive force applied to the sensor assembly 700 is distributed across the back plate 750, the domed loading disc 760, and the outer portion 706 of the beam structure 770, thereby limiting, preventing, or otherwise inhibiting additional deflection of the arm portions 712.

Referring again to FIGS. 1-2, and with continued reference to FIGS. 7-8, in accordance with one embodiment, sensor assembly 110 is realized as the sensor assembly 700 of FIGS. 7-8. As described above, the back plate 750 may be affixed, adhered, mounted, or otherwise mechanically coupled to the bottom surface 138 of the drive system 108 such that the sensor assembly 700 and the drive system 108 are concentrically aligned in the axial direction 118. When the drive system 108 drives the slide 106 forward into the reservoir 105 in the axial direction 118, fluid pressure increases, producing a reactionary force on the drive system 108 in the opposite direction which is transferred to the back plate 750. The capping member 112 prevents displacement of the sensor assembly 700 and effectively maintains the loading disc 760 and/or dowel member 728 in a fixed position with respect to the capping member 112 and/or housing 102. As a result, the reactionary force is transferred to the beams 702 by the loading disc 760 and/or rim portion 736 of the dowel member 728. In this manner, the capping member 112 is configured to deflect the beams 702 towards the surface 710 of the back plate 750 in response to the force provided by the drive system 108 in the axial direction 118. The deflection of the beams 702 is correlated with the axial force applied to the sensor assembly 700 and produces a corresponding increase in the strain exerted upon sensing elements 704. As set forth above, the control electronics 124 are electrically coupled to the sensing elements 704 and configured to determine the force provided or otherwise applied by the drive system 108 in the axial direction 118 based on electrical signals obtained from the sensing elements 704.

Referring now to FIGS. 3-8, in accordance with one or more embodiments, the loading disc 360 of the sensor assembly 300 may be realized as the domed loading disc 760 described above in the context of FIGS. 7-8. In such embodiments, the separation distance provided by airgap 780 may be substantially equal to the separation distance provided by the airgap 322 between the end portions 314 of the beam structure 370 and the surface 310 of the back plate 350. In such embodiments, in response to a compressive force applied to the sensor assembly exceeding the intended measurement range, the shoulder portion 764 of the domed loading disc 760 contacts the outer portion 306 of the beam structure 370 and the end portions 314 of the beams 302 contact the back plate 350 substantially simultaneously to distribute the load evenly across the beam structure 370.

Third Embodiment

Figure 9:
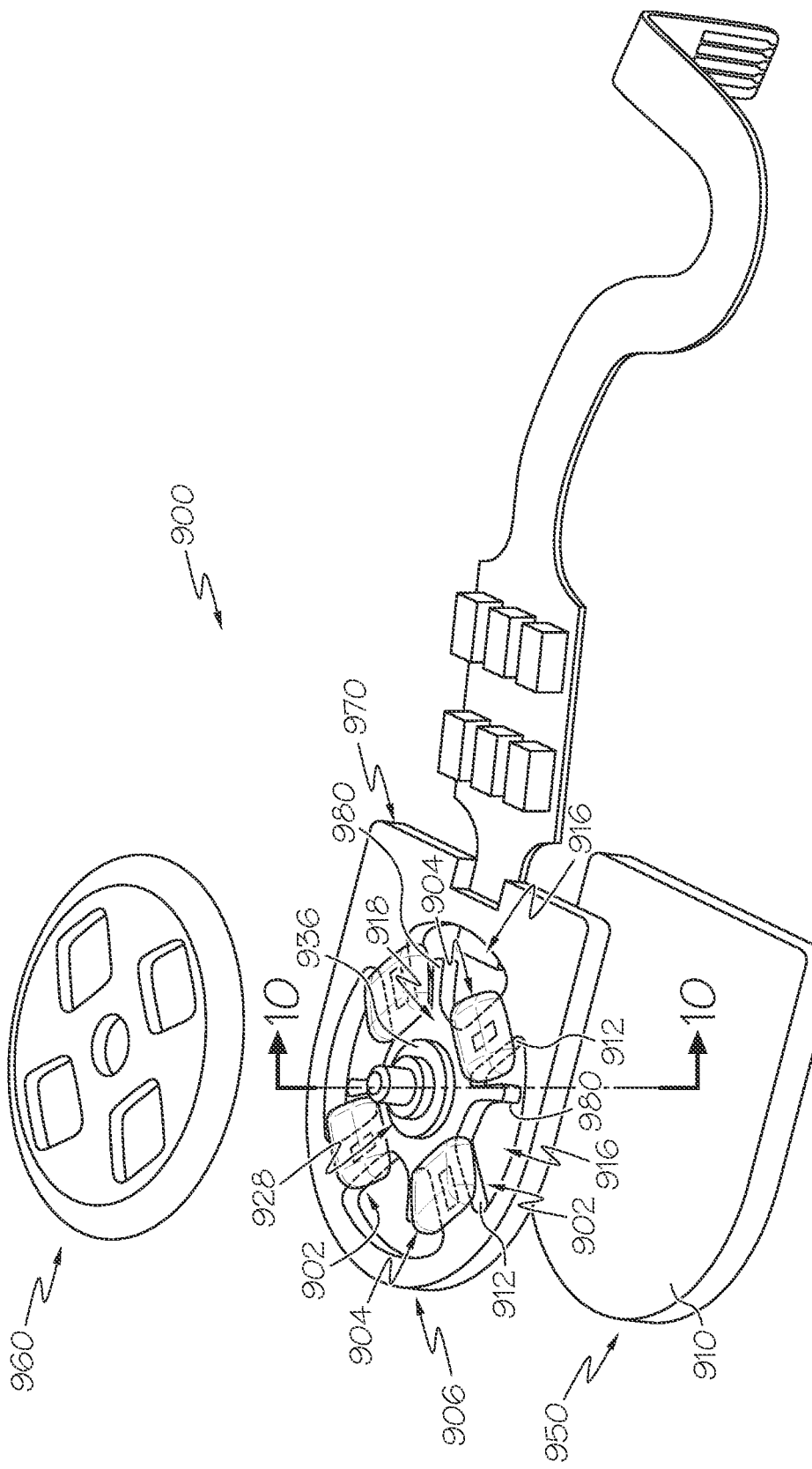
FIG. 9 is an exploded perspective view of an another embodiment of a sensor assembly suitable for use with the infusion pump of FIG. 1.
Figure 10:
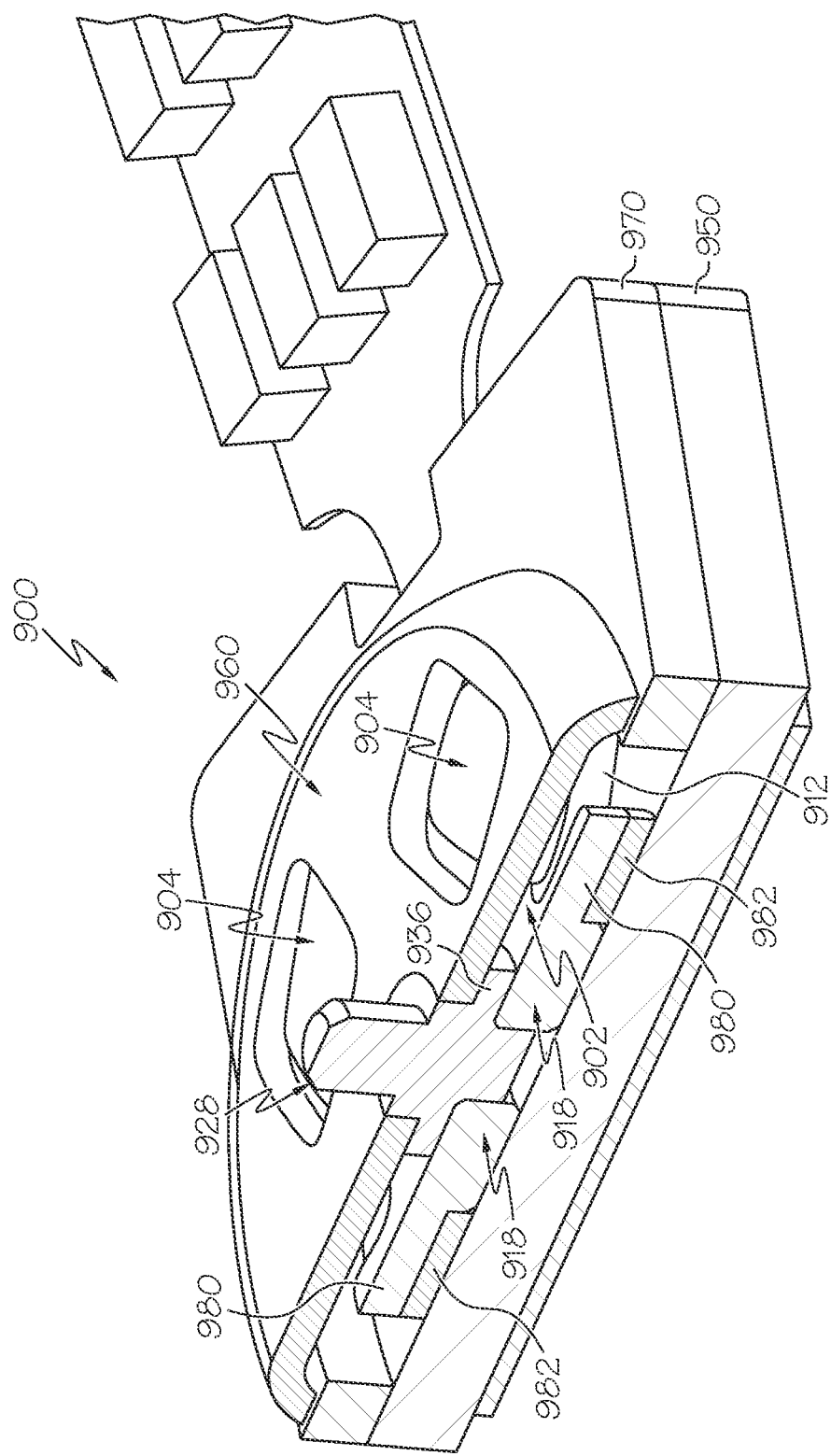
FIG. 10 is a cross-sectional view of the sensor assembly of FIG. 9 illustrating a cross-section as viewed along line 10-10 in FIG. 9.

FIGS. 9-10 depict another exemplary embodiment of a sensor assembly 900 suitable for use as the sensor assembly 110 of FIG. 1. The illustrated embodiment of the sensor assembly 900 includes a loading structure 960 (also referred to herein as a loading element), a back plate structure 950 (or back plate), and a beam structure 970 disposed between the back plate 950 and the loading element 960. Various elements of sensor assembly 900 are similar to counterpart elements described above in the context of sensor assembly 300 of FIGS. 3-6, and the common features of such elements will not be redundantly described here in the context of FIGS. 9-10. As described above in the context of FIGS. 3-6, the beam structure 970 includes one or more beams 902 mechanically coupled to the loading element 960, such that a compressive force applied to the loading element 960 towards the back plate 950 deflects the beams 902 towards the back plate 950. Each beam 902 has a sensing element 904 disposed thereon, wherein an electrical characteristic of the sensing element 904 is influenced by the amount of deflection of the respective beam 902, and thus, is indicative of the force applied to the sensor assembly 900. As described in greater detail below, the beam structure 970 includes cantilevered portions 980 configured to dampen or otherwise absorb impulse forces applied to the sensor assembly 900 that may otherwise result in potentially damaging deflection of the beams 902, for example, during a drop or shock condition.

As illustrated in FIGS. 9-10, the outer portion 906 of the beam structure 970 is disposed adjacent to and in contact with the planar surface 910 of the back plate 950, and the outer portion 906 may be affixed, adhered, welded or otherwise mounted to the planar surface 910 about the periphery of the back plate 950 to provide a supported portion of the beam structure 970 in a similar manner as described above in the context of FIGS. 3-6. Each beam 902 comprises an arm portion 912 of the beam structure 970 that extends radially inward from the outer portion 906 to an end portion. In the illustrated embodiment, the end portions of the beams 902 are integral to form an inner portion 918 of the beam structure 970 that is coaxially aligned with a drive system (e.g., drive system 108 in the axial direction 118). Voided regions 916 physically separate arm portions 912 of adjacent beams 902, and the arm portions 912 are configured to provide voided regions between the beams 902 and the surface 910 of the back plate 950 such that the arm portions 912 are physically separated from the back plate 950. In the absence of a compressive force applied to the back plate 950 and/or loading element 960, the inner portion 918 (i.e., the end portions of the beams 902) does not contact the back plate 950 and the beams 902 are freestanding, detached, or otherwise separated from the back plate 950. In a similar manner as described above, the inner portion 918 includes a circular opening adapted to receive a dowel member 928 that mechanically couples the end portions of the beams 902 to the loading element 960. A rim portion 936 of the dowel member 928 overlaps the inner portion 918 of the beam structure 970 to prevent displacement of the dowel member 928 and/or loading element 960 towards the back plate 950 with respect to the inner portion 918 and distribute a compressive force applied to the sensor assembly 900 across the beams 902 in a substantially even manner.

In the illustrated embodiment of FIGS. 9-10, the beam structure 970 includes a plurality of cantilevered portions 980 that extend radially outward from the inner portion 918 of the beam structure 970. As described in greater detail below, the cantilevered portions 980 are configured to dampen impulse forces applied to the sensor assembly 900 by dampening, retarding or otherwise slowing the rate of displacement of the inner portion 918, which in turn, reduces the rate of deflection of the beams 902. As best illustrated in FIG. 9, the cantilevered portions 980 protrude into the voided regions 916 between adjacent beams 902. In this regard, the cantilevered portions 980 are separated from arm portions 912 of adjacent beams 902 by portions of the voided regions 916. In an exemplary embodiment, the beam structure 970 includes the same number of beams 902 and cantilevered portions 980, such that each arm portion 912 is located between two adjacent cantilevered portions 980 while each cantilevered portion 980 is located between two adjacent arm portions 912. The cantilevered portions 980 are also separated from the outer portion 906 of the beam structure 970 by the voided regions 916, such the cantilevered portions 980 are movable with respect to the outer portion 906. In this regard, the radial length of the cantilevered portions 980 is less than the radial length of the arm portions 912. By virtue of their separation from the outer portion 906 and arm portions 912, the cantilevered portions 980 move in unison with the inner portion 918 and/or end portions of the beams 902 with respect to the outer portion 906.

As illustrated in FIG. 10, in an exemplary embodiment, the cantilevered portions 980 include a dampening material 982 configured to dampen, retard, or otherwise impede displacement of the inner portion 918 and/or end portions of the beams 902 with respect to the outer portion 906, and thereby mitigate or otherwise reduce the rate of deflection of the arm portions 912 of the beams 902. In an exemplary embodiment, the dampening material 982 is affixed to the lower surface of the cantilevered portions 980 and disposed between the lower surface of the cantilevered portions 980 and the surface 910 of the back plate 950. In the illustrated embodiment, the dampening material 982 contacts the surface 910 of the back plate 950, wherein the rigidity of the back plate 950 inhibits or otherwise prevents displacement of the dampening material 982, and as a result, the dampening material 982 absorbs impulse forces applied to the sensor assembly 900. In this manner, the dampening material 982 and cantilevered portions 980 protect the sensing elements 904 and the beams 902 from potentially damaging deflection that may otherwise result from compressive impulse forces that exceed the intended measurement range.

By virtue of the separation between the cantilevered portions 980 and the beams 902 and/or arm portions 912, the dampening material 982 does not influence deflection of the beams 902 and/or arm portions 912 when compressive forces within the intended measurement range are gradually applied to the sensor assembly 900. In this regard, the dampening material 982 and the cantilevered portions 980 are configured such that in response to compressive forces within the intended measurement range applied to the sensor assembly 900, any influence on the deflection of the beams 902 and/or the displacement of inner portion 918 attributable the cantilevered portions 980 and/or dampening material 982 is negligible. Thus, the beams 902 are freely movable (or deflectable) with respect to the back plate 950, and the inner portion 918 may be displaced with respect to the outer portion 906 towards the back plate 950 with negligible dampening or resistance attributable to the cantilevered portions 980 and/or dampening material 982, resulting in applied forces within the intended measurement range being effectively transferred directly to the beams 902.

Referring again to FIGS. 1-2, and with continued reference to FIGS. 9-10, in accordance with one embodiment, sensor assembly 110 is realized as the sensor assembly 900 of FIGS. 9-10. As described above, the back plate 950 may be affixed, adhered, mounted, or otherwise mechanically coupled to the bottom surface 138 of the drive system 108 such that the sensor assembly 900 and the drive system 108 are concentrically aligned in the axial direction 118. When the drive system 108 drives the slide 106 forward into the reservoir 105 in the axial direction 118, fluid pressure increases, producing a reactionary force on the drive system 108 in the opposite direction which is transferred to the back plate 950. The capping member 112 prevents displacement of the sensor assembly 900 and effectively maintains the loading disc 960 and/or dowel member 928 in a fixed position with respect to the capping member 112 and/or housing 102. As a result, the reactionary force is transferred to the beams 902 by the loading disc 960 and/or rim portion 936 of the dowel member 928. In this manner, the capping member 112 is configured to deflect the beams 902 towards the surface 910 of the back plate 950 in response to the force provided by the drive system 108 in the axial direction 118. The deflection of the beams 902 is correlated with the axial force applied to the sensor assembly 900 and produces a corresponding increase in the strain exerted upon sensing elements 904. As set forth above, the control electronics 124 are electrically coupled to the sensing elements 904 and configured to determine the force provided or otherwise applied by the drive system 108 in the axial direction 118 based on electrical signals obtained from the sensing elements 904.

Referring now to FIGS. 3-6 and FIGS. 9-10, in accordance with one or more exemplary embodiments, the beam structure 370 of the sensor assembly 300 may include cantilevered arm portions 980 and dampening material 982 described above in the context of FIGS. 9-10. In such embodiments, when a compressive force applied to the sensor assembly 300 is within the intended measurement range, the cantilevered portions 980 and dampening material 982 negligibly influence displacement of the end portions 314 and/or deflection of the beams 302, and thus, do not influence force measurements obtained using sensing elements 304. In response to an impulse force applied to the sensor assembly, the cantilevered portions 980 and dampening material 982 dampen, retard, or otherwise impede additional displacement of the end portions 314 and/or deflection of the beams 302 towards the back plate 350, and thereby protect the sensing elements 304 and/or the beams 302 from potentially damaging deflection that may otherwise result from compressive impulse forces exceeding the intended measurement range.

Referring again to FIGS. 9-10, in accordance with one alternative embodiment, the thickness of the dampening material 982 may be chosen such that the dampening material 982 does not contact the surface 910 of the back plate 950 in response to compressive forces applied to the sensor assembly 900 that are within the intended measurement range for the sensor assembly 900. In such embodiments, any airgap separating the dampening material 982 from the surface 910 of the back plate 950 is less than the separation distance between the inner portion 918 and the surface 910 of the back plate 950, thereby allowing the dampening material 982 to contact the surface 910 of the back plate 950 before the inner portion 918 and/or end portions of the beams 902 contact the back plate 950. In this regard, when the force applied to the sensor assembly 900 meets or exceeds the upper end of the intended measurement range, the dampening material 982 dampens, retards, or otherwise impedes displacement of the end portions of the beams 902 (i.e., inner portion 918) towards the back plate 950, thereby reducing the rate of displacement of the inner portion 918 and/or end portions of the beams 902 before the inner portion 918 and/or end portions of the beams 902 contact the back plate 950. In other words, the cantilevered portions 980 and dampening material 982 slow the rate of deflection of the beams 902 before the end portions of the beams 902 contact the surface 910 of the back plate 950.

In accordance with another alternative embodiment, the cantilevered portions 980 may be substantially rigid and configured to contact the surface 910 of the back plate 950 to inhibit, prevent, or otherwise limit displacement of the inner portion 918 when the compressive force exceeds the intended measurement range for the sensor assembly 900. In such an embodiment, the separation distance between the cantilevered portions 980 and the surface 910 of the back plate 950 may be chosen such that the cantilevered portions 980 do not contact the surface 910 of the back plate 950 in response to compressive forces applied to the sensor assembly 900 that are within the intended measurement range for the sensor assembly 900. In such embodiments, any airgap separating the cantilevered portions 980 from the surface 910 of the back plate 950 is less than the separation distance between the inner portion 918 and the surface 910 of the back plate 950, such that the cantilevered portions 980 contact the surface 910 of the back plate 950 before the inner portion 918 and/or end portions of the beams 902 contact the back plate 950. As a result, in response to a compressive force applied to the sensor assembly 900 exceeding the intended measurement range, the rigid cantilevered portions 980 contact the back plate 950 to inhibit or otherwise prevent further displacement of the inner portion 918 with respect to the outer portion 906, thereby inhibiting or preventing additional deflection of the arm portions 912 of the beams 902, in a similar manner as described above in the context of FIGS. 3-6. It should be noted that in such alternative embodiments, the cantilevered portions 980 need not include the dampening material 982 to inhibit or prevent displacement of the inner portion 918.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the use of the sensor assembly 300 is not limited to the infusion pumps and drive systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A portable medical device comprising:
    a sensor assembly comprising:
        a beam having an end portion;
        a sensing element disposed on the beam;
        a structure to prevent deflection of the beam; and
        a loading element coupled to the end portion, wherein the end portion is configured to contact the structure when a force applied to the loading element toward the structure is greater than a threshold value;
    a sliding member; and
    a drive system to displace the sliding member in a first direction, the sensor assembly being coupled to the drive system to measure the force provided by the drive system to displace the sliding member in the first direction.

2. The portable medical device of claim 1, the beam comprising an arm portion, wherein a separation distance between the end portion and the structure is less than a separation distance between the arm portion and the structure.

3. The portable medical device of claim 1, wherein the beam is affixed to the structure such that the end portion of the beam is freestanding with respect to the structure.

4. The portable medical device of claim 1, wherein an electrical characteristic of the sensing element is influenced by deflection of the beam.

5. The portable medical device of claim 1, wherein:
    the structure comprises a planar surface;
    the beam comprises a supported portion coupled to the planar surface; and
    the end portion that is freestanding with respect to the structure.

6. The portable medical device of claim 5, the beam comprising an arm portion between the supported portion and the end portion, wherein the sensing element is disposed on the arm portion.

7. The portable medical device of claim 6, wherein:
    a separation distance between the end portion and the planar surface is less than a separation distance between the arm portion and the planar surface; and
    the end portion contacts the planar surface of the structure to prevent deflection of the arm portion when the force applied to the loading element is greater than the threshold value.

8. The portable medical device of claim 6, wherein the sensing element comprises a strain-sensitive element having a glass coating affixing the strain-sensitive element to the arm portion.

9. The portable medical device of claim 1, wherein:
the threshold value is between 5.0 pounds and 10.0 pounds; and
the sensing element measures force applied to the sensor assembly that is less than the threshold value with a resolution less than or equal to 0.01 pounds.

10. The portable medical device of claim 1, further comprising a capping member to prevent displacement of the sensor assembly in a second direction opposite the first direction, wherein the sensor assembly is positioned between the drive system and the capping member.

11. A sensor assembly, comprising:
a beam structure comprising a plurality of beams, each beam of the plurality of beams having an end portion;
a plurality of sensing elements, each sensing element of the plurality of sensing elements being disposed on a respective beam of the plurality of beams;
a structure to prevent deflection of one or more beams of the plurality of beams; and
a loading element coupled to the end portions, wherein the end portion of a first beam of the plurality of beams is configured to contact the structure when a force applied to the loading element toward the structure is greater than a threshold value.

12. The sensor assembly of claim 11, wherein the end portions of the plurality of beams are integral.

13. The sensor assembly of claim 12, wherein;
the beam structure comprises a supported portion affixed to the structure; and
each beam of the plurality of beams comprises an arm portion extending from the supported portion to its respective end portion.

14. The sensor assembly of claim 13, wherein a separation distance between the end portions and the structure is less than a separation distance between the arm portions and the structure.

15. The sensor assembly of claim 13, wherein the end portions are freestanding with respect to the structure.

16. The sensor assembly of claim 13, wherein the arm portions extending radially inward from the supported portion to the end portions to form an inner portion of the beam structure.

17. The sensor assembly of claim 16, further comprising a dowel member including a rim portion to mechanically couple the end portions and the loading element and separate the loading element from the arm portions of the plurality of beams.

18. The sensor assembly of claim 17, the inner portion including a first opening and the loading element including a second opening, wherein the dowel member includes a cylindrical portion having a first end inserted in the first opening and an opposing end protruding through the second opening.

19. A sensor assembly, comprising:
a beam structure comprising a plurality of beams, the beam structure including an outer portion, each beam of the plurality of beams including an arm portion extending radially inward from the outer portion to an end portion, the end portions being integral to form an inner portion of the beam structure;
a plurality of sensing elements, each sensing element of the plurality of sensing elements being disposed on a respective beam of the plurality of beams;
a structure to prevent deflection of one or more beams of the plurality of beams; and
a loading element mechanically coupled to the inner portion, the beam structure being disposed between the loading element and the structure, wherein the inner portion is configured to contact the structure when a compressive force applied to the loading element toward the structure is greater than a threshold value.

20. The sensor assembly of claim 19, further comprising a dowel member comprising:
a rim portion to mechanically couple the end portions and the loading element and separate the loading element from the arm portions of the plurality of beams; and
a cylindrical portion having a first end inserted in an opening in the inner portion and an opposing end protruding through an opening in the loading element.

* * * * *